(12) United States Patent
Kwon et al.

(10) Patent No.: US 7,572,595 B2
(45) Date of Patent: Aug. 11, 2009

(54) METHOD FOR SEARCHING MYELIN USING GONADOTROPIN-RELEASING HORMONE RECEPTORS AS A NEW BIOMARKER

(75) Inventors: Oh-Seung Kwon, Seoul (KR); Euna Park, Seoul (KR); Heesoo Pyo, Seoul (KR); Yong-Ho Huh, Yongin-si (KR)

(73) Assignee: Korea Institute of Science and Technology, Seoul (KR)

( * ) Notice: Subject to any disclaimer, the term of this patent is extended or adjusted under 35 U.S.C. 154(b) by 322 days.

(21) Appl. No.: 11/277,836

(22) Filed: Mar. 29, 2006

(65) Prior Publication Data
US 2007/0099243 A1    May 3, 2007

(30) Foreign Application Priority Data
Oct. 27, 2005    (KR)    ............... 10-2005-0101846

(51) Int. Cl.
*G01N 33/53* (2006.01)
*G01N 33/535* (2006.01)
*G01N 33/541* (2006.01)
*G01N 33/566* (2006.01)

(52) U.S. Cl. ............... 435/7.1; 435/7.5; 435/334; 436/501

(58) Field of Classification Search ............... None
See application file for complete search history.

(56) References Cited

OTHER PUBLICATIONS ncbi.nlm.nih.gov/entrez/viewer.fcgi?db=protein&id=399777; 8 pages: downloaded Sep. 27, 2008.*
Peter et al., General and Comparative Endocrinol. 2003; 132: 399-408.*
Millar et al., Journal of Endocrinol. 1999; 162: 117-126.*
Jacobson, Jill D., "Gonadotropin-releasing hormone: potential role in autoimmunity," International Immunopharmacology, 1:1077-1083 (2001).
Igaz et al., "Effects of Cytokines on Gonadotropin-Releasing Hormone (GnRH) Gene Expression in Primary Hypothalamic Neurons and in GnRH Neurons Immortalized Conditionally," Endocrinology, 147(2):1037-1043 (2006).
Jacobson et al., "Gender-Specific Exacerbation of Murine Lupus by Gonadotropin-Releasing Hormone: Potential Role of $G\alpha_{q/11}$," Endocrinology, 140(8):3429-3437 (1999).

* cited by examiner

*Primary Examiner*—Bridget E Bunner
*Assistant Examiner*—Christina Borgeest
(74) *Attorney, Agent, or Firm*—Joseph Hyosuk Kim; JHK Law

(57) ABSTRACT

The present invention relates to a method for searching myelin using gonadotropin-releasing hormone receptors (GnRH-R) as a biomarker, more precisely, a method for investigating the distribution of myelin by immunohistochemical staining using GnRH-R antibody, based on the fact that GnRH-R and myelin are observed in the same region. The method for searching myelin of the invention can contribute to the studies on demyelination related degenerative brain disease and the disclosure of functions of myelin and the relation of myelin and GnRH-R.

3 Claims, 9 Drawing Sheets

GnRH-R

CNP

LFB

GnRH-R

CNP

METHOD FOR SEARCHING MYELIN USING GONADOTROPIN-RELEASING HORMONE RECEPTORS AS A NEW BIOMARKER

TECHNICAL FIELD

The present invention relates to a method for searching myelin using gonadotropin-releasing hormone receptors (GnRH-R) as a biomarker, more precisely, a method for investigating the distribution of myelin by immunohistochemical staining using GnRH-R antibody, based on the fact that GnRH-R and myelin are observed in the same region.

BACKGROUND ART

Gonadotropin-releasing hormone (GnRH) is secreted in hypothamaus and transmitted to pituitary, where the hormone is specifically linked to a high affinity receptor which exists on the cell membrane of pituitary to interact with each other. GnRH is secreted in the hypothamaus by means of a pulse pattern. In fact, every normal physiological synthesis and secretion-related reactions are involved in pulse mode reaching a receptor (Belchetz P E et al., Science 202, 631-633, 1978).

Human GnRH receptor (GnRH-R) gene is composed of three exons and two introns (Fan N C et al., Moll. Cell. Endocrinol. 107, R1-R8, 1995), which enables various splicing or transmission of variants, suggesting the diversity in its function. GnRH and GnRH-R are found in major lymphatic organs or immune cells including lymphocytes (Standaert F E et al., Biol. Reprod., 46, 997-1000, 1992). GnRH-R is found in not only testis or ovary (Botte M C et al., J. Endocrinol. 159, 179-189, 1998), in addition to pituitary, but also pituitary adenoma secreting growth hormone, progesterone or thyroid-stimulating hormone (Rosa S L et al., Virchows Arch., 437, 264-269, 2000). Although the physiological functions of GnRH-R in the pituitary of the central nervous system (CNS) have been well known, the other functions in other regions have been hardly disclosed.

Myelin is an extended cell membrane of a fat-rich oligodendrocyte or Schwann cell covering the axon of a neuron, which has a function of transmitting nerve impulse by action potential to other neurons or muscle junctions of motor neurons. Considering the ratio between major components of myelin, the percentage of lipid is characteristically high over protein. In particular, protein takes 30% of the total weight of dried myelin found in human or rodent brains and the remaining 70% is consisted of lipid components. Myelin found in CNS is composed of 28% cholesterol, 28% glycolipid and 43% phospholipids. Glycolipid and sphingolipid take 35% of the total lipid.

It has been known that myelin in CNS has more than 40 enzyme activities, based on which it is understood that the function of myelin as an electric insulator is characterized by an active metabolism resulted by a unique enzyme activity. Besides, the membrane of myelin harbors muscarinic receptors (Larocca J N et al., J. Neurosci., 7, 3863-3876, 1987) or G-protein receptors (Larocca J N et al., J. Neurochem., 57, 30-38, 1991), indicating that myelin is capable of transmitting a signal.

Myelin is found in rather white matter than gray matter of CNS, which are confirmed by staining methods such as Busch's method, Loyez's method and Luxol fast blue method, etc. It is also possible to use a protein component of myelin such as 2',3'-cyclic nucleotide 3'-phosphodiesterase (CNP), myelin-associated glycoprotein, myelin basic protein, galactocerobroside, myelin oligodendrocyte glycoprotein and proteolipid protein, as a marker for searching myelin with immunohistochemical staining (Trapp B D et al., Cell biology of myelin assembly, In: Myelin biology and Disorders, edited by Lazzarini R A et al., p. 29-55, Elsevier Academic Press, Amsterdam, 2004; Sospedra M. and Martin R, Ann. Rev. Immunol., 23, 638-747, 2005).

Examples of the use of a specific protein as a searching marker include Korean Patent No. 10-2005-0052754 which describes the use of PrxII protein as a marker for searching vascular endothelial cells and a composition for searching vascular endothelial cells containing an antibody against PrxII protein. However, the use of GnRH-R as a marker for searching a specific region or a specific material, especially myelin, has not been reported in any scientific literature, yet.

The present inventors observed GnRH-R in the same region where myelin is found, and then suggested the usability of GnRH-R as a new marker for searching myelin. The present inventors further completed the invention by confirming that GnRH-R can be effectively used for the treatment of myelin-related diseases including demyelination-related degenerative brain disease.

DISCLOSURE

Technical Problem

It is an object of the present invention to examine whether the distribution of GnRH-R is consistent with the distribution of myelin by using myelin specific staining method and immunohistochemical method and to provide a method for searching myelin by using GnRH-R as a new marker.

Technical Solution

To achieve the above object, the present invention provides a biomarker for searching myelin containing GnRH-R and a method for searching myelin using the same.

The present invention also provides a kit for searching myelin containing anti-GnRH-R antibody.

Hereinafter, the present invention is described in detail.

The present invention provides a biomarker for searching myelin containing gonadotropin-releasing hormone receptor (GnRH-R) and a method for searching myelin using the same.

The method for searching myelin of the invention using GnRH-R as a new biomarker is composed of following steps:

1) Preparing tissue samples;
2) Reacting the samples with anti-GnRH-R antibody and washing thereof;
3) Reacting the washed tissues of step 2) with a color coupler linked secondary antibody and washing thereof;
4) Inducing color development by adding a substrate reactive to the color coupler to the samples of step 3); and
5) Observing the prepared slides under a microscope.

In step 1), the preparation of tissue samples can be performed by the conventional method well-known to those in the art, for example, taking a sample, fixing, embedding and preparing sample sections, etc. To prepare samples in an exemplary embodiment of the invention, a brain section with abundant myelin distribution was used. However, there is no limitation in tissues to be used for searching myelin and every tissue of a target area can be used.

In step 2), the anti-GnRH-R antibody can be purchased or produced by the conventional method widely used in the field of immunology. For example, GnRH-R protein is dissolved in phosphate buffered saline, to which a required amount of Freund's complete adjuvant is added, followed by emulsification. The resultant emulsion is hypodermically injected at one week interval and immunization is induced by several times of injection. The antibody titer is measured. The additional injection is performed at the highest titer, and then blood samples are taken at proper time point. The obtained antiserum is fractionally precipitated using ammonium sulfate. The globulin fraction was purified by anion-exchange chromatography or the antiserum is diluted with binding buffer. The diluted antiserum is purified by protein A or protein G sepharose column chromatography, resulting in the anti-GnRH-R protein polyclonal antibody.

Anti-GnRH-R monoclonal antibody can also be prepared by the conventional method well-known to those in the field of immunology. Particularly, a mouse or a rat is immunized with GnRH-R, and then the immunized lymphocytes are fused to myeloma cells to form hybridoma by the conventional method known to those in the art. From the hybridoma culture solution, antibody-producing hybridoma recognizing each antigen by solid phase ELISA using a highly purified antigen is selected. After cloning the obtained hybridoma, a stable antibody-producing hybridoma is selected for further culture. At last, a target antibody is obtained. GnRH-R protein to be used for the production of the above antibody is separated from nature resources or can be produced by a genetic recombination method (Chapter 4. Antibodies: Structure and Function, In *Immunology*, Edited by R. A. Goldsby et al., W.H. Freeman and Company, Basingstroke, England, 2003).

A color coupler linked to the secondary antibody can be selected from a group consisting of HRP (horseradish peroxidase), alkaline phosphatase, colloid gold, biotin, fluorescein such as FITC (fluorescein isothiocyanate), RITC (rhodamine-B-isothiocyanate) and rhodamine, enzyme, metal and dye.

In step 3), the substrate inducing color development is preferably selected according to a marker, and is exemplified by DAB (diaminobenzidine tetrahydrochloride), TMB (3,3', 5,5'-tetramethylbezidine), ABTS [2,2'-azino-bis(3-ethylbenzothiazoline-6-sulfonic acid)], OPD (o-phenylenediamine), AEC (3-amino-9-ethyl carbazole), 4CN (4-chloro-1-naphthol), benzidine dihydrochloride, silver particle, etc.

The present inventors investigated the distribution of myelin after staining myelin by immunohistochemical method using anti-GnRH-R antibody or 2'3'-cyclic nucleotide 3'-phosphodiesterase (CNP) antibody and Luxol fast blue method. Then, the results were compared. Based on the results, the inventors suggested the usability of GnRH-R as a new marker for searching myelin. Anti-CNP immunohistochemical staining was performed according to the method of Nishizawa et al. (Nishizawa Y et al., *Neurochemical Research*, 10, 1107-1118, 1985) with a slight modification. Luxol fast blue staining was performed according to the method of Margolisand Pickett (Margolis G and Pickett J P, *Lab. Invest.*, 5, 459-474, 1956) with a slight modification. As a result, the result of searching myelin by using GnRH-R as a biomarker was consistent with that of the conventional staining method, indicating that GnRH-R can be effectively used as a myelin marker. The above results were confirmed again by fluorescent staining (FIG. 8 and FIG. 9).

Myelin associated diseases, in particular, diseases mediated by demyelination are exemplified by ischemic demyelination, inflammatory demyelination and leukoencephalopathy. The method for searching myelin of the invention can be effectively used for the pathological studies for such diseases.

The present invention further provides a kit for searching myelin containing anti-GnRH-R antibody.

The kit of the invention contains, in addition to the anti-GnRH-R antibody, a color coupler linked secondary antibody and a substrate for successful performance of immunohistochemical staining, which can be used for myelin-related pathological studies, histopathological diagnosis, determination of a treatment method and decision of prognosis.

DESCRIPTION OF DRAWINGS

The application of the preferred embodiments of the present invention is best understood with reference to the accompanying drawings, wherein.

Figure 1:
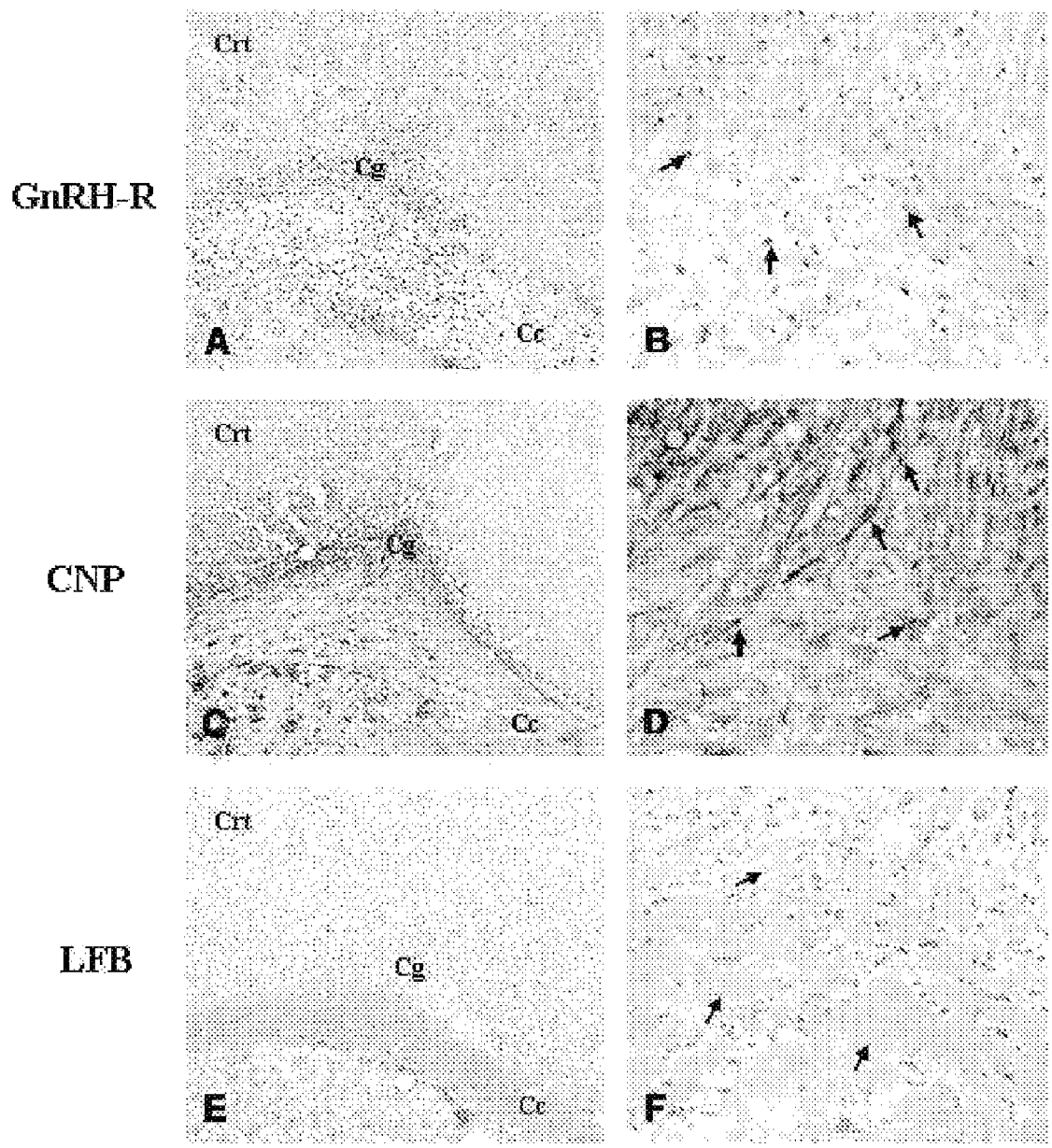
FIG. 1 is a set of microphotographs showing the distribution of myelin in the corpus callosum and cingulum of the forebrain of a mouse, A, B: GnRH-R immunohistochemical staining C, D: CNP immunohistochemical staining E, F: Luxol fast blue (LFB)

Magnification: A, C, E: ×100; B, D, F: ×400

Cc: Corpus callosum, Cg: Cingulum, Crt: Cortex (Staining method and magnification of A~F are same.)

FIGS. 2A-F are a set of photomicrographs showing the distribution of myelin in the caudate putamen of the forebrain of a mouse.

FIGS. 3A-F are a set of photomicrographs showing the distribution of myelin in the corpus callosum and cingulum of the hindbrain of a mouse.

FIGS. 4A-F are a set of photomicrographs showing the distribution of myelin in the stria medullaris of thalamus of the hindbrain of a mouse.

FIGS. 5A-F are a set of photomicrographs showing the distribution of myelin in the fimbria of hippocampus of the hindbrain of a mouse.

FIGS. 6A-F are a set of photomicrographs showing the distribution of myelin in the internal capsule of the hindbrain of a mouse.

FIGS. 7A-F are a set of photomicrographs showing the distribution of myelin in the optic tract of the hindbrain of a mouse.

FIGS. 8A-D are a set of photomicrographs showing the colocalization of GnRH-R and CNP in myelin regions of the corpus callosum and cingulum.

A, B: GnRH-R immunohisto staining

C, D: CNP immunohisto staining

Magnification: A, C: ×i00; B, D: ×400

Cc: Corpus callosum, Cg: Cingulum, Crt: Cortex

Hp: field CA1 of hippocampus

FIGS. 9A-D are a set of photomicrographs showing the colocalization of GnRH-R and CNP in myelin region of the optic tract of mice brains.

A, B: GnRH-R immunohistochemical staining

C, D: CNP immunohistochemical staining

Magnification: A, C: ×i00; B, D: ×400

Opt: optical tract.

MODE FOR INVENTION

Practical and preferred embodiments of the present invention are illustrative as shown in the following Examples.

However, it will be appreciated that those skilled in the art, on consideration of this disclosure, may make modifications and improvements within the spirit and scope of the present invention.

Experimental Example 1

Anti-CNP Immunohistochemical Staining

Anti-CNP immunohistochemical staining was performed according to the method of Nishizawa et al. (Nishizawa Y et al., *Neurochemical Research*, 10, 1107-1118, 1985) with a slight modification. Particularly, a mouse (C57/BL6, female, 18-20 g, 6-8 weeks old) was anesthetized with 4% chloral hydrate (10 mL/kg; Sigma), and the brain was fixed by perfusing 4% paraformaldehyde/0.1 M phosphate buffer (pH 7.4) to the heart by using a peristaltic pump (Masterflex™, Barnant Co.). The brain was separated, followed by post-fixation in the same solution at 4° C. for 24 hours. Then, the brain was stored in 20% sugar/0.1 M phosphate solution for overnight, followed by sectioning (40 μm) the brain using Vibratome 1000 Plus™ (Vibratome). The sections were stored in a 24 well-plate containing 0.1% sodium azide/0.1 M phosphate buffer at 4° C. until use.

The brain tissue section was washed with 50 mM Tris-HCl (pH 7.4) and then stood for 30 minutes at room temperature in 0.5% $H_2O_2$/Tris-HCl solution (pH 7.4). The section was washed with Tris-HCl solution (pH 7.4) three times for 5 minutes per each time, and then reacted in 0.5% triton-X/50 mM Tris-HCl solution (pH 7.4) for 25 minutes. The section was washed by the same manner as described above. The section was cultured in 10% normal horse serum (Gibco-BRL)/3% bovine serum albumin (Sigma)/0.1% triton-X in 50 nM Tris-HCl solution (pH 7.4) for 2 hours, followed by washing with Tris-HCl solution three times for 5 minutes each.

Goat mouse anti-CNP antibody (1:100, Chemicon) was added thereto, which was cultured in 1.5% normal horse serum/0.3% triton-X in 50 mM Tris-HCl solution (pH 7.4) for 1-4 hours at room temperature, followed by reaction at 4° C. for overnight. After washing three times with Tris-HCl solution for 5 minutes per each time, the section was reacted with goat anti-mouse serum (1:1000, Chemicon) for one hour at room temperature, followed by washing again. The section was reacted with streptavidin horse-radish peroxidase in Tris-HCl (50 mM) solution (1:100, Silenus) for one hour at room temperature. After washing, color development was induced for 2-5 minutes by using DAB kit solution (1:10, diaminobenzidine tetrahydrochloride kit, Roche).

Experimental Example 2

Luxol Fast Blue Staining

Luxol fast blue staining was performed according to the method of Margolis and Pickett (Margolis G and Pickett J P, *Lab. Invest.*, 5, 459-474, 1956) with a slight modification. Particularly, a mouse (C57/BL6, female, 18-20 g, 6-8 weeks old) was anesthetized with 4% chloral hydrate (10 mL/kg; Sigma), and the brain was fixed by perfusing 4% paraformaldehyde/0.1 M phosphate buffer (pH 7.4) to the heart by using a peristaltic pump (Masterflex™, Barnant Co.). The brain was separated, followed by post-fixation in the same solution at 4° C. for 24 hours. Then, the brain was stored in 20% sugar/0.1 M phosphate solution for overnight, followed by sectioning (40 μm) by using Vibratome 1000 Plus™ (Vibratome). The sections were stored in a 24 well-plate containing 0.1% sodium azide/0.1 M phosphate buffer at 4° C. until use.

The brain tissue section was dried on a slid glass, and then reacted serially in 95% ethanol for one minute, in 0.1% luxol fast blue solution (Sigma) at room temperature for overnight and by heating at 70° C. for 5 hours. The fraction was washed in 95% ethanol and in distilled water serially, followed by contacting to 0.05% carbonated lithium solution for one minute for further reaction. After standing in 70% ethanol for one minute, the section was washed with distilled water. The section was contacted with 0.05% carbonated lithium solution for one minute until blue color in gray matter was gone. Then, the section was left in 70% ethanol for one minute, followed by washing with distilled water (approximately takes one hour). Then, the section was reacted in 0.1% cresyl violet (Sigma) for one minute, followed by washing with distilled water for 30 seconds. Dehydration was performed serially with 80%, 90% and 100% ethanol. The section was covered by a cover-glass, followed by observation under a microscope.

Example 1

GnRH-R Immunohistochemical Staining

A mouse (C57/BL6, female, 18-20 g, 6-8 weeks old) was anesthetized with 4% chloral hydrate (10 mL/kg; Sigma), and the brain was fixed by perfusing 4% paraformaldehyde/0.1 M phosphate buffer (pH 7.4) to the heart by using a peristaltic pump (Masterflex™, Barnant Co.). The brain was separated, followed by post-fixation in the same solution at 4° C. for 24 hours. Then, the brain was stored in 20% sugar/0.1 M phosphate solution for overnight, followed by sectioning (40 μm) by using Vibratome 1000 Plus™ (Vibratome). The sections were stored in a 24 well-plate containing 0.1% sodium azide/ 0.1 M phosphate buffer at 4° C. until use.

The brain tissue section was washed with 50 mM Tris-HCl (pH 7.4) and then stood for 30 minutes at room temperature in 0.5% $H_2O_2$/Tris-HCl solution (pH 7.4). The section was washed with Tris-HCl solution (pH 7.4) three times for 5 minutes per each time, and then reacted in 0.5% triton-X/50 mM Tris-HCl solution (pH 7.4) for 25 minutes. The section was washed by the same manner as described above. The section was cultured in 10% normal horse serum/3% bovine serum albumin/0.1% triton-X in 50 mM Tris-HCl solution (pH 7.4) for 2 hours, followed by washing with Tris-HCl solution three times for 5 minutes each. The section was reacted in goat anti-human anti-GNRH-R antibody (sc-8682, 1:500, Santa Cruz)/Tris-HCl solution containing 1.0% bovine serum albumin for 12 hours at 4° C. without culturing at room temperature. After washing with Tris-HCl solution three times for 5 minutes each, the section was reacted in donkey anti-goat horse-radish peroxidase IgG)/Tris-HCl solution containing 1.0% bovine serum albumin (1:500, Santa Cruz) for one hour at room temperature. After washing, color development was induced for 2-5 minutes by using DAB kit solution (1:10, diaminobenzidine tetrahydrochloride kit, Roche).

<1-1> Staining of Myelin in the Corpus Callosum and Cingulum of a Mouse Forebrain GnRH-R was distributed widely in corpus callosum callosum (Cc) and cingulum (Cg) of a mouse forebrain, confirmed by GnRH-R immunohistochemical staining (FIG. 1). The result was consist with the distribution of CNP, known as a myelin searching marker, or the result of Luxol fast blue staining, a myelin specific staining method. While it was apparently observed by CNP or LFB staining that myelin in Cg included nerve fibers, GnRH-R staining only confirmed the small and round-shaped structures. That means that GnRH-R staining can show the distribution of myelin more effectively than other staining methods and GnRH-R itself is abundant in oligodendrocytes. In the meantime, the purple regions in LFB staining (E, F) indicate cell bodies of neurons stained by cresyl violet.

<1-2> Staining of Myelin in the Caudate Putamen of a Mouse Forebrain

Figure 2:
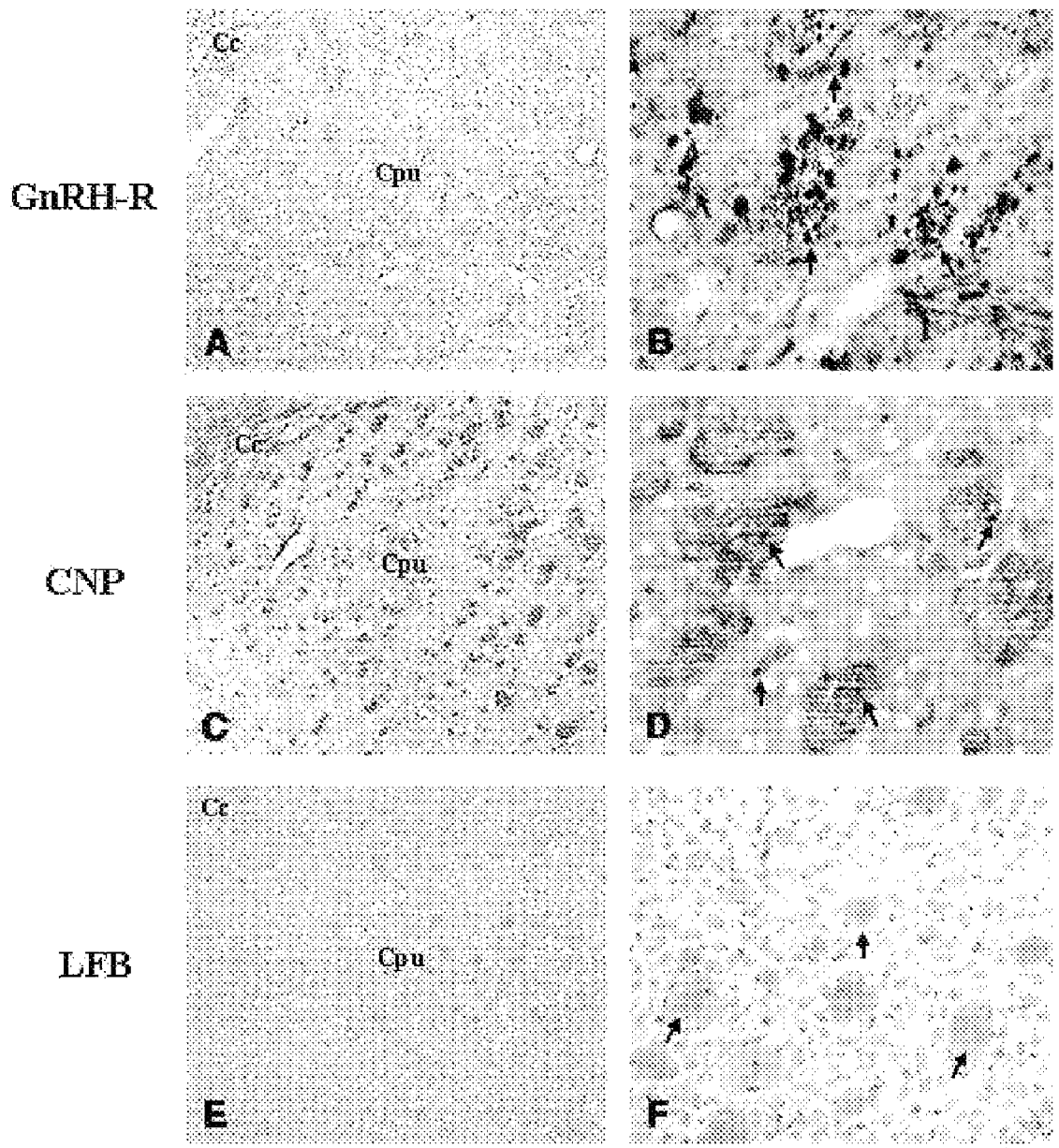

The results of staining of GnRH-R, CNP and LFB in the caudate putamen of a mouse forebrain are shown in FIG. 2. Staining of GnRH-R, CNP and LFB all proved that myelin fiber bundles (A, C, E) are abundant in the caudate putamen of the forebrain, and GnRH-R and CNP staining further showed round-shaped myelin regions (B, D) between fiber bundles. GnRH-R staining showed the similar result to CNP staining, but GnRH-R could show a darker and bigger region. That means that the sensitivity of GnRH-R staining is higher than that of other staining methods, suggesting that GnRH-R staining can stain myelin more clearly.

Figure 3:
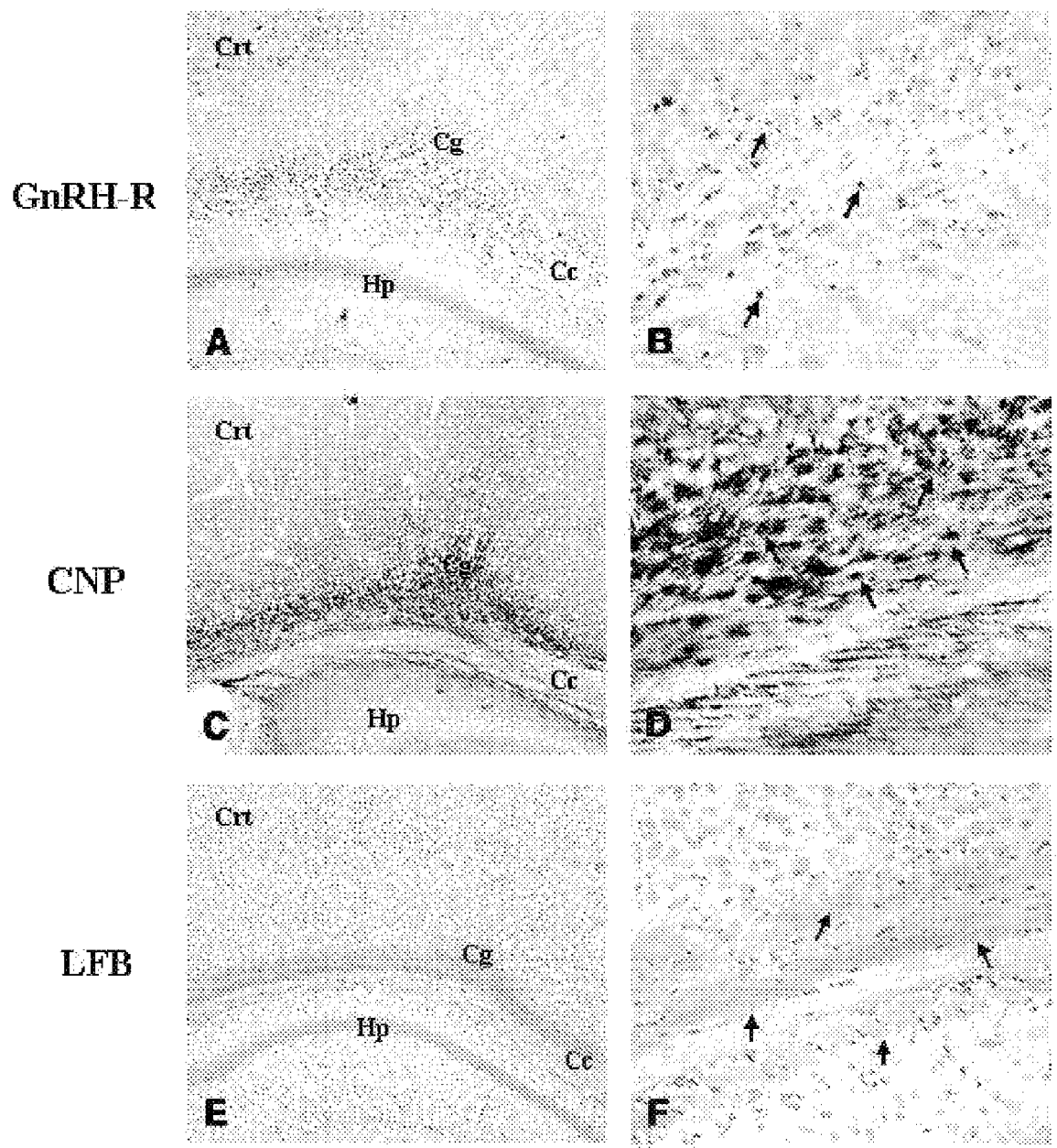

<1-3> Staining of Myelin in the Corpus Callosum and Cingulum of a Mouse Hindbrain (FIG. 3)

In large, it is the same region as FIG. 1, but precisely, it is a little bit behind from the region of FIG. 1, which is corresponding to the plates 33-34 of a cross section of the brain (Sterotaxic map) (Paxinos G and Watson C, The rat brain in stereotaxic coordinates, 4th ed., Academic press, 1998). The results of each staining of GnRH-R, CNP and LFB are similar and myelin rich regions are widely stained. Staining of myelin in cingulum by CNP, LFB and GnRH-R were compared and as a result, GnRH-R staining region was wider and the band of myelin track was also widely distributed. Besides, in cingulum region, filament-like fibriform myelin was not clear by the GnRH-R staining, but widely distributed small and round-shape structures were observed. The distribution of myelin in the hippocampus was not clearly detected in a microphotograph, either. The distribution of GnRH-R was closer to that of CNP than to that of LFB.

Figure 4:
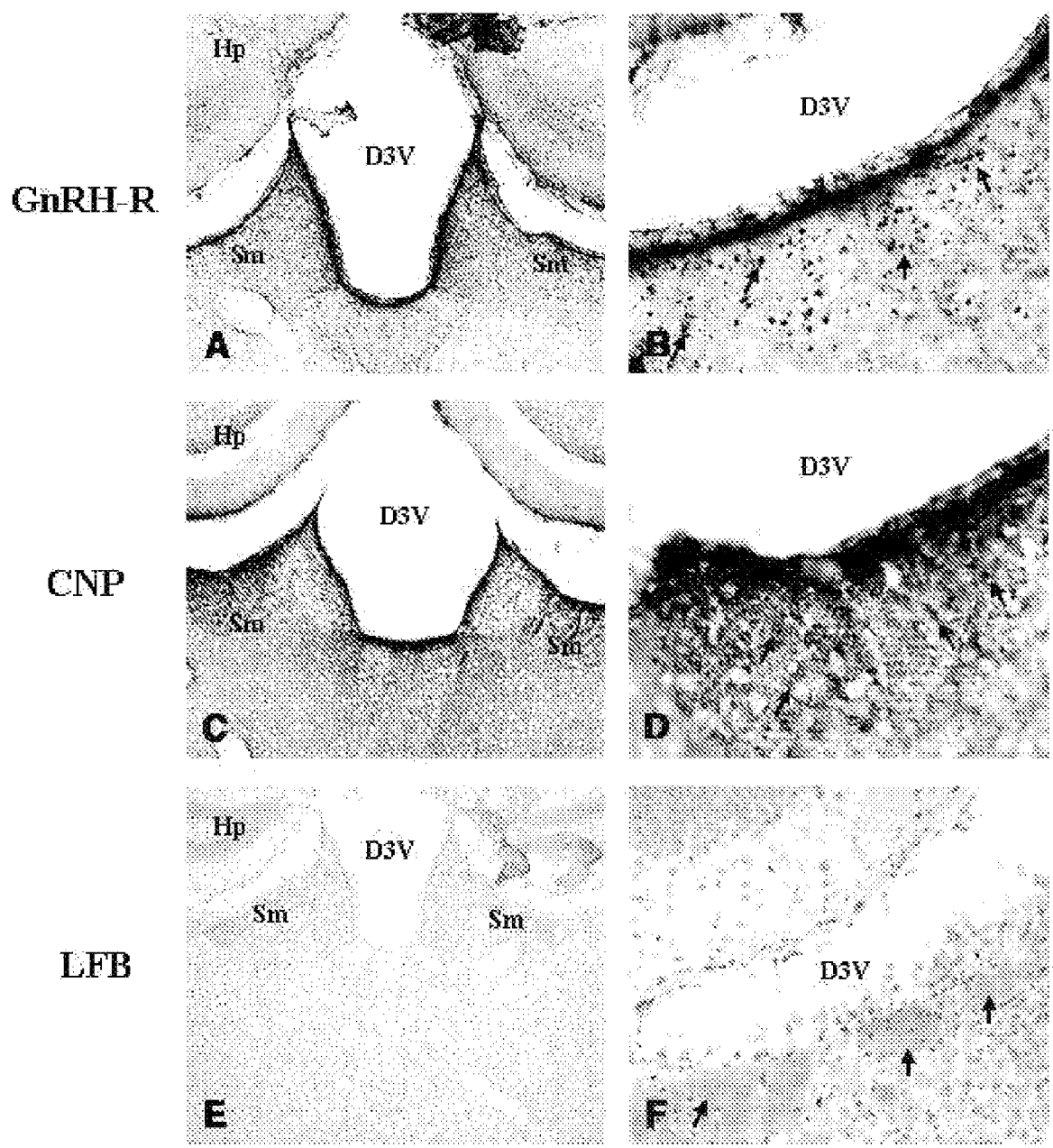

<1-4> Staining of Myelin in the Stria Medullaris of Thalamus of a Mouse Hindbrain (FIG. 4)

The results of GnRH-R, CNP and LFB staining in the stria medullaris of thalamus adjacent to the third cerebral ventricle are shown in FIG. 4. Myelin was not detected in hippocampus by the staining using those three markers, as known so far, and the distribution of myelin in gray matter was also poor.

Figure 5:
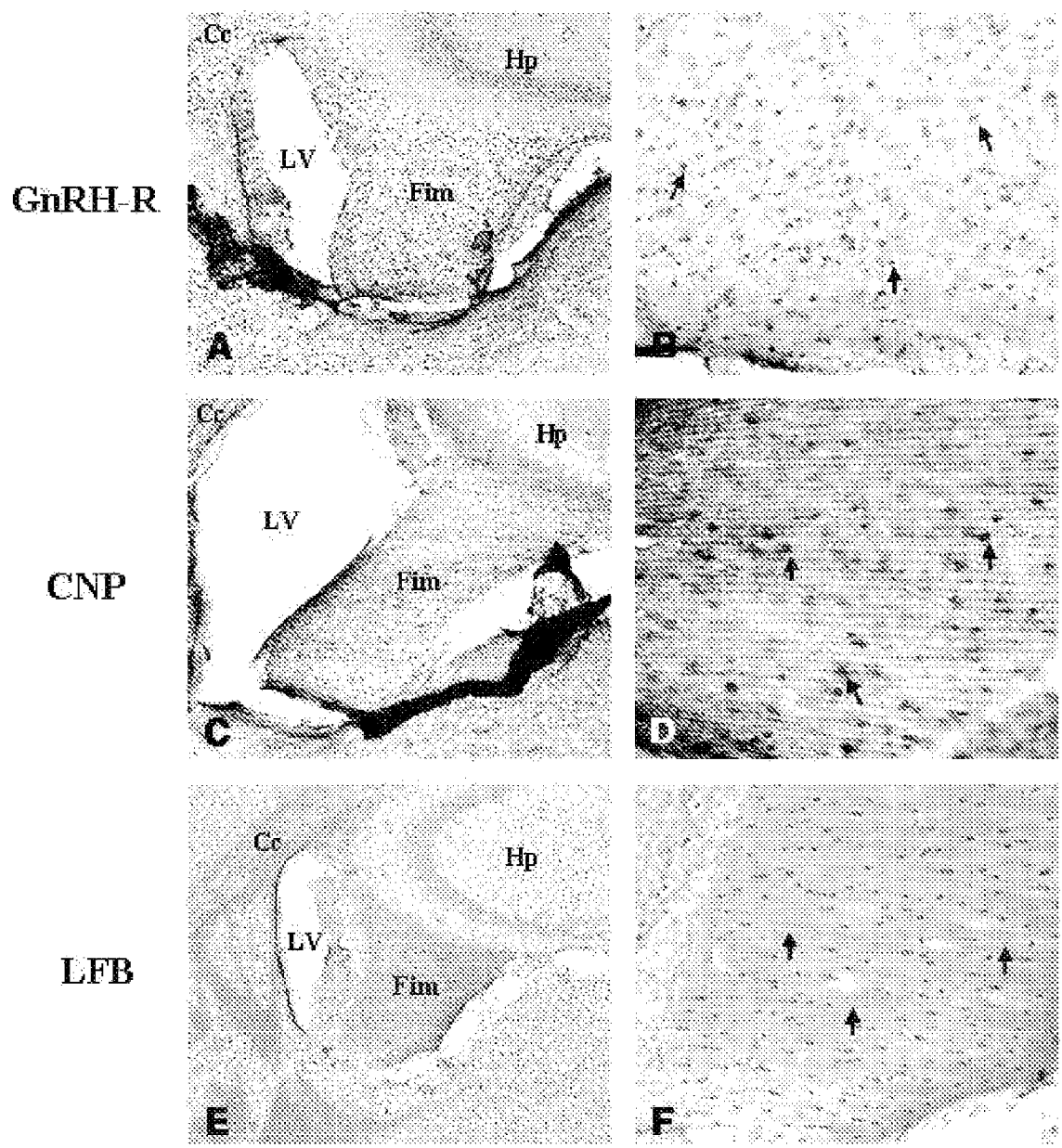

<1-5> Staining of Myelin in the Fimbria of Hippocampus of a Mouse Hindbrain (FIG. 5)

The results of GnRH-R, CNP and LFB staining in the fimbria of hippocampus are shown in FIG. 5. The distribution of myelin in the fimbria of hippocampus was more clearly detected by GnRH-R or LFB staining than CNP staining. The fimbria of hippocampus has been known as a myelin rich-region, along with corpus callosum or optic tract (Schmued L C *J. Histochem. Cytochem.,* 38, 717-720, 1990).

Figure 6:
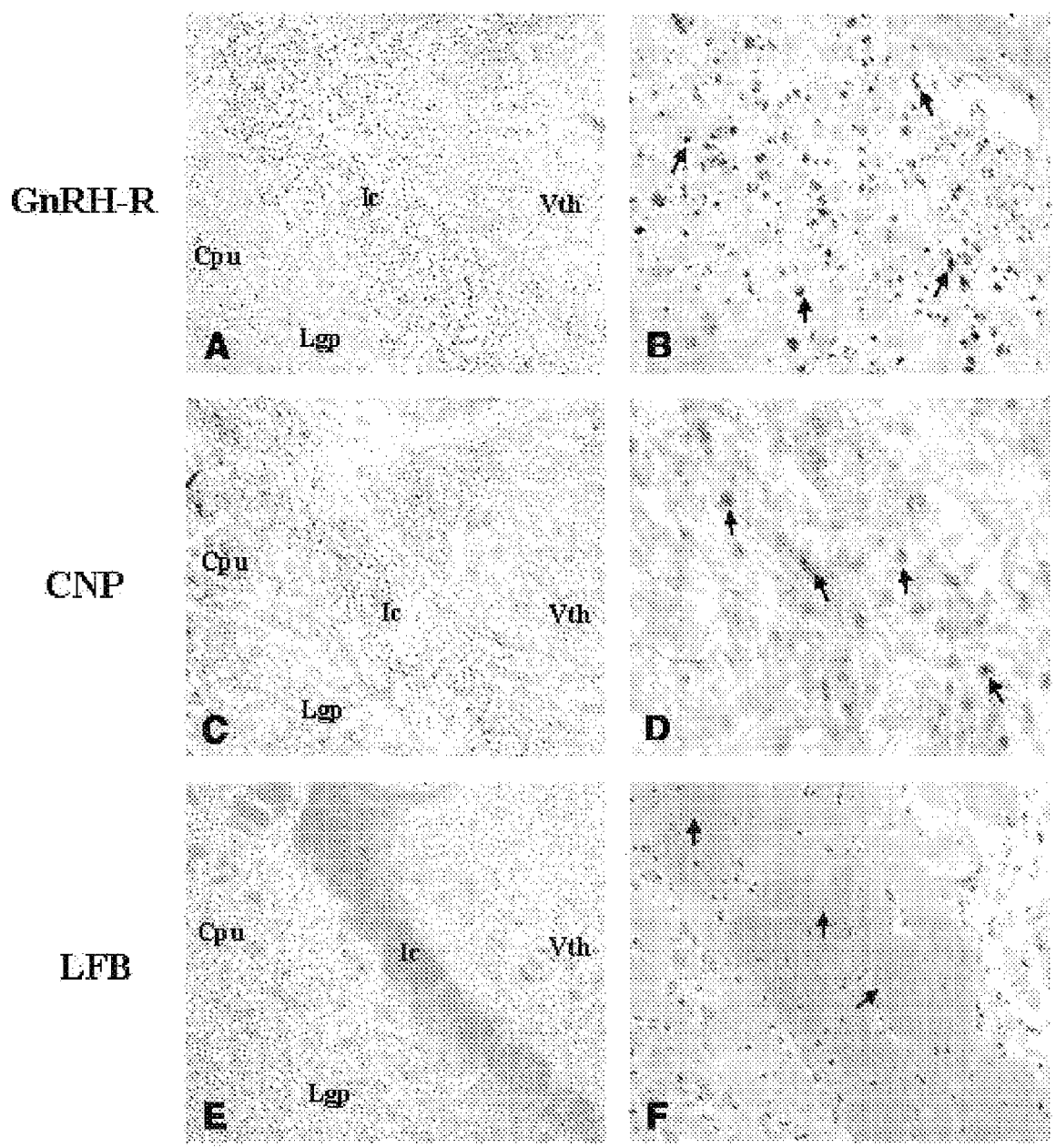

<1-6> Staining of Myelin in the Internal Capsule of a Mouse Hindbrain (FIG. 6)

The results of GnRH-R, CNP and LFB staining in the internal capsule are shown in FIG. 6. GnRH-R staining showed more apparent and crowded distribution of myelin, compared with the CNP staining. In particular, GnRH-R antibody was more clearly stained than CNP. By using LFB, myelin containing region was stained evenly with equal density.

Figure 7:
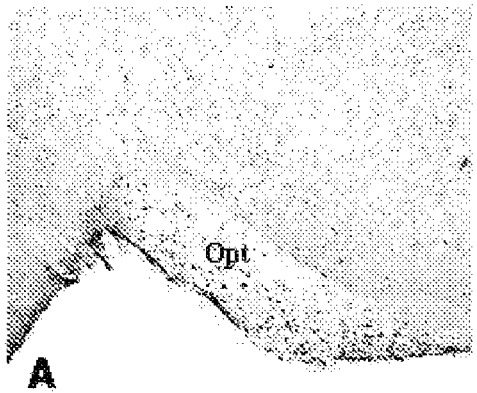
Figure 7:
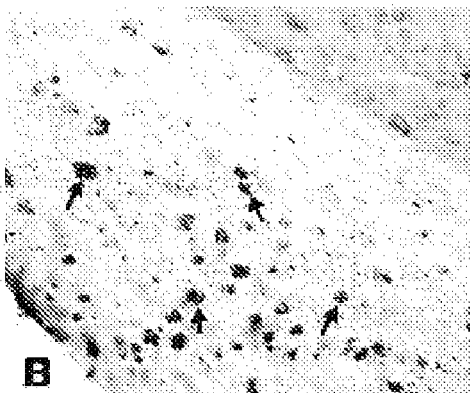
Figure 7:
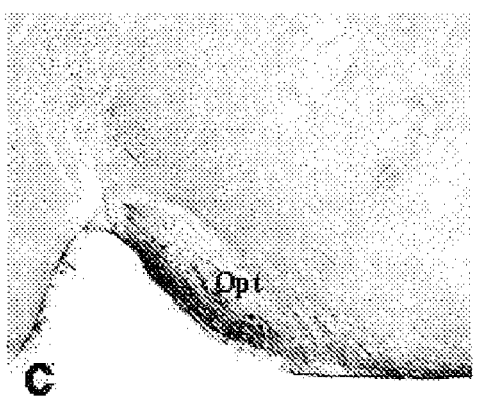
Figure 7:
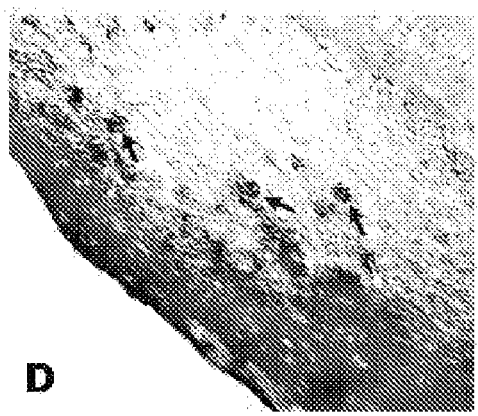
Figure 7:
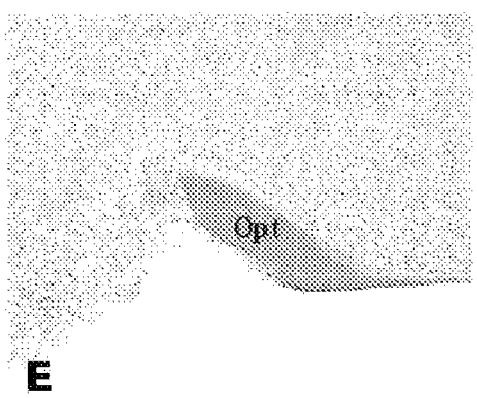
Figure 7:
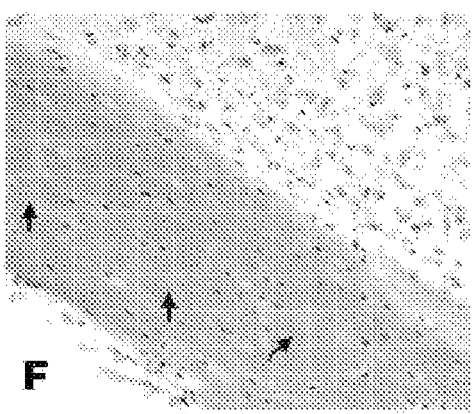
Figure 8:
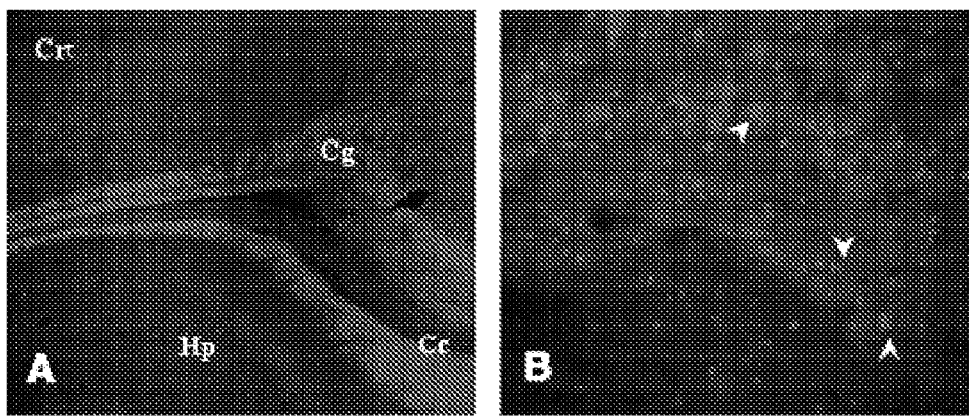
Figure 8:
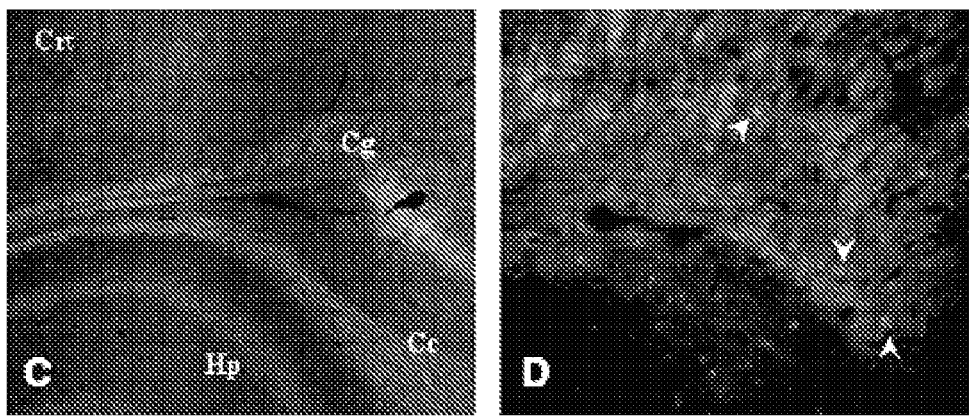
Figure 9:
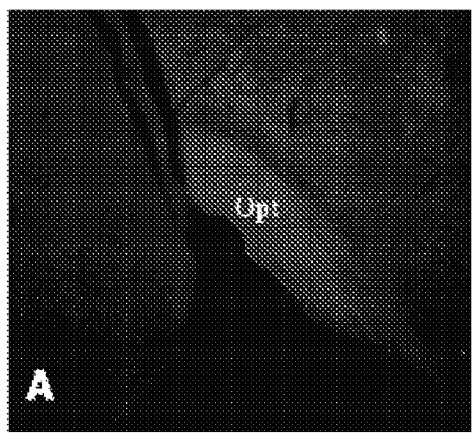
Figure 9:
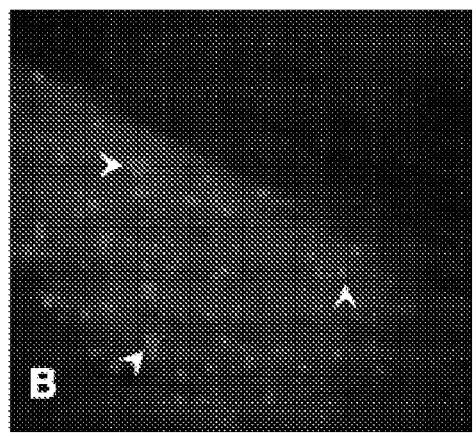
Figure 9:
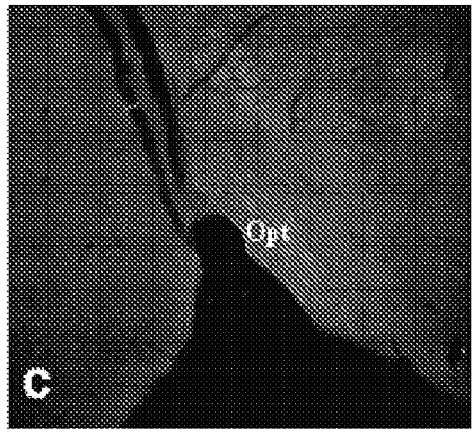
Figure 9:
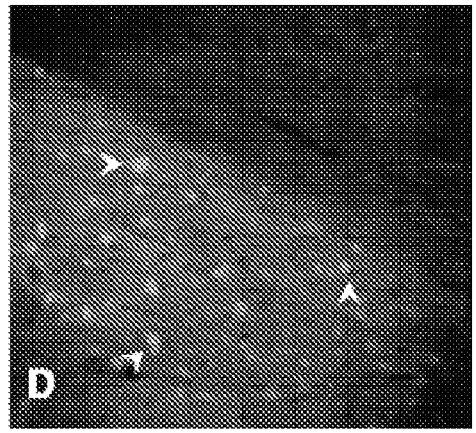

<1-7> Staining of Myelin in the Optic Tract of a Mouse Hindbrain (FIG. 7)

The results of GnRH-R, CNP and LFB staining in the optic track are shown in FIG. 7. GnRH-R in optic tract was stained much stronger than those in corpus callosum, cingulum, fimbria of hippocampus and internal capsule. In the meantime, LFB rather stained the entire region of optic tract, suggesting that GnRH-R is more myelin-specific than other two markers.

As explained hereinbefore, a method for searching myelin using GnRH-R as a biomarker can exhibit the distribution of myelin in the brain more precisely with stronger staining.

Example 2

Double Fluorescent Staining of GnRH-R and CNP

The processes before primary antibody reaction were the same as described above, and after the same pretreatment, the section was reacted in goat anti-human GnRH-R antibody (se-8682, 1:500, Santa Cruz) and chicken anti-CNP antibody (1:50, Chemicon, Temecular)/Tris-HCl solution (pH 7.4) containing 1% bovine serum albumin for 72 hours at 4° C. without incubation at room temperature. After washing with Tris-HCl solution three times for 5 minutes each, the section was reacted in donkey anti-goat IgG (Rhodamine) and rabbit anti-chicken IgY (FITC)/Tris-HCl solution containing 1.0% bovine serum albumin (1:500, Santa Cruz) for one hour at room temperature. After washing, the sample was placed on a slide and dehydrated, which was covered by a cover-glass, followed by observation under a microscope.

<1-1> Fluorescent Staining of Myelin in Corpus Callosum and Cingulum

FIG. 1 and FIG. 3 show the myelin rich-regions of the forebrain and the hindbrain. As being consistent with the results of immunohistochemical staining using GnRH-R, CNP and LFB, colocalization of GnRH-R and CNP was confirmed by double fluorescent staining, and precisely, GnRH-R shown between myelin track and round-shaped myelin was clearer than CNP.

<1-2> Fluorescent Staining of Myelin in the Optic Tract of a Mouse Hindbrain

Colocalization of GnRH-R and CNP was observed in the optic track, one of myelin-rich regions showing a bigger round shaped myelin. GnRH-R was clearly stained where CNP expression was observed, by which colocalization of GnRH-R and myelin was confirmed.

As explained hereinbefore, the results of fluorescent staining strongly support the results of immunohistochemical staining using GnRH-R, CNP and LFB. Thus, it was confirmed that the method of the invention for searching myelin using GnRH-R as a biomarker is very effective.

INDUSTRIAL APPLICABILITY

As explained hereinbefore, a novel method for searching myelin by using GnRH-R as a biomarker exhibits the distribution of myelin more exactly and precisely, compared with the conventional methods using other markers. The existence of GnRH-R in a myelin-containing region was not reported so far. Therefore, the method of the invention using GnRH-R as a biomarker can contribute to studies on the physiological functions of GnRH-R, the demyelination-related degenerative brain disease caused by multiple sclerosis and heavy metal intoxication and other myelin related studies in the field of neuroscience or neurotoxicology. It is further expected that GnRH-R marker can be applied to the diagnosis of the demyelination-related degenerative brain disease.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A method for examining the distribution of myelin in tissue samples using gonadotropin-releasing hormone receptor (GnRH-R) as a biomarker comprising the following steps:
   (i) preparing myelin rich tissue samples, wherein the samples are selected from the group consisting of corpus callosum, cingulum, fimbria of hippocampus, internal capsule, stria medullaris of thalamus and optic tract;
   (ii) reacting the samples with an anti-GnRH-R antibody and washing the samples;
   (iii) reacting the washed samples of step (ii) with a color coupler linked secondary antibody, washing the samples and placing on a slide;
   (iv) inducing color development by adding a substrate reactive to the color coupler to the samples of step (iii); and
   (v) observing the prepared slides under a microscope for positive staining of GnRH-R wherein positive staining for GnRH-R indicates the distribution of myelin in tissues samples.

2. The method according to claim 1, wherein the color coupler of step iii) is selected from the group consisting of HRP (horseradish peroxidase), alkaline phosphatase, colloid gold, biotin, FITC (fluorescein isothiocanate), RITC (rhodamine-B-isothiocyanate) and rhodamine B.

3. The method according to claim 1, wherein the substrate of step iv) is selected from a group consisting of DAB (diaminobenzidine tetrahydrochloride), TMB (3,3',5,5'-tetramethylbezidine), ABTS [2,2'-azino-bis (3-ethylbenzothiazoline-6-sulfonic acid)], OPD (o-phenylenediamine), AEC (3-amino-9-ethyl carbazole), 4CN (4-chloro-l-naphthol), benzidine dihydrochloride and silver particle.

* * * * *